United States Patent
Akashi et al.

(10) Patent No.: US 8,207,379 B2
(45) Date of Patent: Jun. 26, 2012

(54) RUTHENIUM COMPOUND AND METHOD FOR PRODUCING OPTICALLY ACTIVE AMINOALCOHOL COMPOUND

(75) Inventors: Masaya Akashi, Naka-gun (JP); Tsutomu Inoue, Chigasaki (JP)

(73) Assignee: Nippon Soda Co., Ltd., Tokyo (JP)

( * ) Notice: Subject to any disclaimer, the term of this patent is extended or adjusted under 35 U.S.C. 154(b) by 52 days.

(21) Appl. No.: 12/936,496

(22) PCT Filed: Apr. 3, 2009

(86) PCT No.: PCT/JP2009/001569
§ 371 (c)(1),
(2), (4) Date: Oct. 5, 2010

(87) PCT Pub. No.: WO2009/125565
PCT Pub. Date: Oct. 15, 2009

(65) Prior Publication Data
US 2011/0028749 A1    Feb. 3, 2011

(30) Foreign Application Priority Data
Apr. 7, 2008  (JP) ................................. 2008-099267

(51) Int. Cl.
C07C 209/00 (2006.01)
C07F 15/00 (2006.01)
(52) U.S. Cl. ......................................... 564/358; 556/22
(58) Field of Classification Search .................... 556/22; 564/358
See application file for complete search history.

(56) References Cited

U.S. PATENT DOCUMENTS

| | | | |
|---|---|---|---|
| 6,218,575 B1 * | 4/2001 | Klingler et al. | ............... 564/358 |
| 6,410,749 B1 | 6/2002 | Katayama et al. | |
| 2001/0037026 A1 | 11/2001 | Crameri et al. | |
| 2003/0045727 A1 | 3/2003 | Nakano et al. | |
| 2008/0027249 A1 | 1/2008 | Puentener et al. | |

FOREIGN PATENT DOCUMENTS

| | | |
|---|---|---|
| JP | 10-130289 | 5/1998 |
| JP | 11-189600 | 7/1999 |
| JP | 2002-284790 | 10/2002 |
| JP | 2005-068113 | 10/2002 |
| WO | WO 02/04401 | 1/2002 |

OTHER PUBLICATIONS

Tani, Kazuhide, et al., "Rh(I) Complexes Containing Fully Alkylated Mono- and Diphosphine Ligands as Highly Active Hydrogenation Catalysts for Carbonyl Compounds", Chemistry Letters, 1982, No. 3, pp. 261-264.

Burk, Mark J., et al., "Efficient Rhodium-Catalyzed Hydrogenation of Aldehydes and Ketones", Tetrahedron Letters, 1994, vol. 35, No. 28, pp. 4963-4966.

Zhang, Xiaoyong, et al., "Asymmetric Hydrogenation of Cycloalkanones Catalyzed by BINAP-Ir(I)-Aminophosphine Systems", Journal of the American Chemical Society, Apr. 21, 1993, vol. 115, No. 8, pp. 3318-3319.

Doucet, Henri, et al., "*trans*-[RuCl$_2$(phosphane)$_2$(1,2-diamine)] and Chiral trans-[RuCl$_2$(diphosphane)(1,2-diamine): Shelf-Stable Precatalysts for the Rapid, Productive, and Stereoselective Hydrogenation of Ketones", Angewandte Chemie International Edition, 1998, vol. 37, No. 12, pp. 1703-1707.

International Search Report, International PCT Application No. PCT/JP2009/001569, mailed Jun. 23, 2009. (Translated).

European Search Report dated Oct. 26, 2011, issued for EP 09730145.1, 5 pages.

\* cited by examiner

*Primary Examiner* — Porfirio Nazario Gonzalez
(74) *Attorney, Agent, or Firm* — Kenyon & Kenyon LLP

(57) ABSTRACT

A novel ruthenium compound that is useful as an asymmetric reduction catalyst for carbonyl compounds. The ruthenium compound of the present invention is represented by a formula (I): $(Ru(X)_2(Pxx)[R^1R^2C(NH_2)-R^3R^4C(NH_2)]$ (I)), and when this compound is used as an asymmetric reduction catalyst, an optically active aminoalcohol compound can be produced from an α-aminoketone, and particularly a compound represented by formula (IV), with high stereoselectivity and high yield.

[Chemical formula 1]

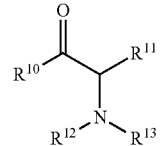

(IV)

9 Claims, No Drawings

RUTHENIUM COMPOUND AND METHOD FOR PRODUCING OPTICALLY ACTIVE AMINOALCOHOL COMPOUND

TECHNICAL FIELD

The present invention relates to a method for producing an optically active aminoalcohol compound by asymmetrically reducing a carbonyl compound, and particularly an α-aminoketone compound, using a novel ruthenium compound that is useful as an asymmetric reduction catalyst for carbonyl compounds, and also relates to the novel ruthenium compound.

Priority is claimed on Japanese Patent Application No. 2008-099267, filed Apr. 7, 2008, the content of which is incorporated herein by reference.

BACKGROUND ART

Conventionally, known methods for producing optically active alcohol compounds have involved the catalytic asymmetric reduction of carbonyl compounds such as ketones. Examples of these known methods include methods using a rhodium complex disclosed in Non-Patent Documents 1 and 2, a method using an iridium complex disclosed in Non-Patent Document 3, a method disclosed in Patent Document 1 that involves performing a hydrogen transfer using ruthenium as a catalyst, and a method disclosed in Patent Document 2 that involves performing a hydrogenation using ruthenium as a catalyst.

However, of these methods, in the methods disclosed in Non-Patent Documents 1 to 3, the metal used as a catalyst is a comparatively expensive so-called noble metal such as rhodium or iridium, which also has a comparatively low hydrogenation activity, and when such a metal is used as an asymmetric reduction catalyst, a comparatively high temperature or high hydrogen pressure is required. In the method disclosed in Patent Document 1, an organic compound such as formic acid must be used as the hydrogen source, and therefore the method is unfavorable from an operational and cost perspective when compared with methods where a cheap hydrogen source such as hydrogen gas can be used. Further, although the method disclosed in Patent Document 2 is a superior asymmetric reduction method for carbonyl compounds, it also suffers from problems, including the fact that favorable results cannot be obtained without using a catalyst having an expensive bidentate phosphine ligand with a plurality of substituents, and a diamine ligand that is difficult to synthesize.

Accordingly, there has been considerable demand for the development of an inexpensive asymmetric hydrogenation catalyst which is capable of using an inexpensive hydrogen source such as hydrogen gas to convert a carbonyl compound to a corresponding optically active alcohol compound with high selectivity and high yield.

A multitude of ruthenium catalysts have already been developed, and of these, representative examples of several ruthenium catalysts having a phosphine ligand, which are the most similar to the present invention, are presented below.

(1) A ruthenium complex represented by formula (1):

[Chemical formula 1]

$$RuXY(PR^1R^2R^3)n(NR^6R^7R^8)m \qquad (1)$$

wherein X and Y may be the same or different, and each represents a hydrogen atom, halogen atom, carboxyl group or other anion group, $R^1$, $R^2$ and $R^3$ may be the same or different, and each represents a hydrocarbon group that may have a substituent, or alternatively, $R^1$ and $R^2$ may be bonded together to form a carbon chain ring that may have a substituent, n represents an integer of 0 to 4, $R^6$, $R^7$ and $R^8$ may be the same or different, and each represents a hydrogen atom or a hydrocarbon group that may have a substituent, and m represents an integer of 0 to 4 (see Patent Document 2).

(2) a ruthenium compound represented by formula (2):

[Chemical formula 2]

$$Ru(X)(Y)(Px)n_1[R^1R^2C*(NR^3R^4)-A-R^5R^6C*(NR^7R^8)] \qquad (2)$$

wherein each of X and Y independently represents a hydrogen atom, halogen atom, carboxyl group, hydroxyl group or C1 to C20 alkoxy group, Px represents a phosphine ligand, each of $R^1$ to $R^8$ independently represents a hydrogen atom, C1 to C20 alkyl group that may have a substituent, C2 to C20 alkenyl group that may have a substituent, C3 to C8 cycloalkyl group that may have a substituent, aralkyl group that may have a substituent, or aryl group that may have a substituent, and either of $R^1$ and $R^2$ may be bonded to either of $R^3$ and $R^4$ to form a ring, either of $R^5$ and $R^6$ may be bonded to either of $R^7$ and $R^8$ to form a ring, A represents a C1 to C3 alkylene that may have a substituent and may have an ether linkage, C3 to C8 cycloalkylene that may have a substituent, allylene that may have a substituent, or divalent hetero ring that may have a substituent, and in those cases where A represents an alkylene group, either of $R^1$ and $R^2$ may be bonded to either of $R^5$ and $R^6$ to form a ring, * indicates an asymmetric carbon atom, and $n_1$ represents an integer of 1 or 2 (see Patent Document 3).

(3) A ruthenium compound represented by formula (3):

[Chemical formula 3]

$$Ru(X)(Y)(Px)n(A) \qquad (3)$$

wherein each of X and Y independently represents a hydrogen atom, halogen atom, carboxyl group, hydroxyl group or C1 to C20 alkoxy group, Px represents a phosphine ligand, n represents 1 or 2, and A represents a diamine ligand represented by formula (4) or formula (5) shown below:

[Chemical formula 4]

$$R^1CH(NH_2)CH_2(NR^2R^3) \qquad (4)$$

$$R^1CH(NR_2R_3)CH_2(NH_2) \qquad (5)$$

wherein $R^1$ represents a C1 to C20 alkyl group that may have a substituent, C2 to C20 alkenyl group that may have a substituent, C3 to C8 cycloalkyl group that may have a substituent, C7 to C20 aralkyl group that may have a substituent, aryl group that may have a substituent, or heterocyclic group, each of $R^2$ and $R^3$ independently represents a hydrogen atom, C1 to C20 alkyl group that may have a substituent, C2 to C20 alkenyl group that may have a substituent, C3 to C8 cycloalkyl group that may have a substituent, or C7 to C20 aralkyl group that may have a substituent, and $R^2$ and $R^3$ may be bonded together to form a ring, provided that $R^2$ and $R^3$ are not both hydrogen atoms (see Patent Document 4).

PRIOR ART DOCUMENTS

Patent Documents

[Patent Document 1]
Japanese Unexamined Patent Application, First Publication No. Hei 10-130289
[Patent Document 2]
Japanese Unexamined Patent Application, First Publication No. Hei 11-189600
[Patent Document 3]
Japanese Unexamined Patent Application, First Publication No. 2002-284790
[Patent Document 4]
Japanese Unexamined Patent Application, First Publication No. 2005-68113

Non-Patent Documents

[Non-Patent Document 1] Chemistry Letters, 1982, p. 261
[Non-Patent Document 2] Tetrahedron Letters, 1994, vol. 35, p. 4963
[Non-Patent Document 3] Journal of American Chemical Society, 1993, vol. 115, p. 3318

DISCLOSURE OF INVENTION

Problems to be Solved by the Invention

An object of the present invention is to provide a method for producing a corresponding optically active aminoalcohol compound with high stereoselectivity and high yield by asymmetrically reducing, in particular, an α-aminoketone compound, using a novel ruthenium compound that is useful as an asymmetric reduction catalyst for carbonyl compounds. Another object of the present invention is to provide the novel ruthenium compound that can be obtained with relative ease.

Means to Solve the Problems

In other words, the present invention relates to:
(1) a ruthenium compound represented by a formula (I):

[Chemical Formula 5]

$$Ru(X)_2(Pxx)[R^1R^2C(NH_2)-R^3R^4C(NH_2)] \quad (I)$$

wherein X represents a halogen atom,
Pxx represents an optically active bidentate phosphine ligand represented by formula (II):

[Chemical formula 6]

$$P(R^5)_2-A-P(R^5)_2 \quad (II)$$

wherein $R^5$ represents a phenyl group that has substituents, represented by formula (III):

[Chemical formula 7]

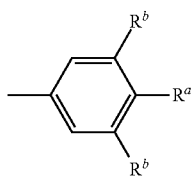

(III)

wherein $R^a$ represents a hydrogen atom, halogen atom, C1 to C6 alkyl group, C1 to C6 alkoxy group or C6 to C18 aryl group, and $R^b$ represents a halogen atom, C1 to C6 alkyl group, C1 to C6 alkoxy group or C6 to C18 aryl group, and A represents a divalent organic group, $R^1R^2C(NH_2)-R^3R^4C(NH_2)$ represents an optically active diamine ligand, in which each of $R^1$ to $R^4$ independently represents a hydrogen atom, unsubstituted or substituted C1 to C20 alkyl group, unsubstituted or substituted C2 to C20 alkenyl group, unsubstituted or substituted C3 to C8 cycloalkyl group, unsubstituted or substituted C4 to C8 cycloalkenyl group, unsubstituted or substituted C6 to C18 aryl group, or unsubstituted or substituted C7 to C18 aralkyl group, and either of $R^1$ and $R^2$ may be bonded to either of $R^3$ and $R^4$ to form a ring.

The present invention also relates to:

(2) a method for producing an optically active aminoalcohol compound by performing a hydrogenation, in the presence of the ruthenium compound described above, of an α-aminoketone compound, and particularly an α-aminoketone compound represented by formula (IV):

[Chemical formula 8]

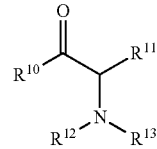

(IV)

wherein each of $R^{10}$ and $R^{11}$ independently represents an unsubstituted or substituted C1 to C6 alkyl group, or unsubstituted or substituted C6 to C18 aryl group, each of $R^{12}$ and $R^{13}$ represents a hydrogen atom, unsubstituted or substituted C1 to C6 alkyl group, unsubstituted or substituted C6 to C18 aryl group, $R^{14}CO-$ group or $R^{14}OCO-$ group, $R^{14}$ represents an unsubstituted or substituted C1 to C6 alkyl group, or unsubstituted or substituted C6 to C18 aryl group, and $R^{10}$ and $R^{11}$, and $R^{12}$ and $R^{13}$, may be respectively bonded together to form a ring.

The method for producing an optically active aminoalcohol compound according to the present invention is preferably:

(3) the method for producing an optically active aminoalcohol compound described in (2) above, wherein $R^{10}$ in formula (IV) is an unsubstituted or substituted phenyl group, (4) the method for producing an optically active aminoalcohol compound described in (2) or (3) above, wherein within the ruthenium compound represented by formula (I), the optically active bidentate phosphine ligand represented by formula (II) is any one of:

an optically active bidentate phosphine ligand represented by formula (II-B):

[Chemical formula 9]

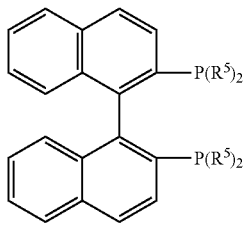

(II-B)

wherein $R^5$ is the same as defined above,
an optically active bidentate phosphine ligand represented by formula (II-C):

[Chemical formula 10]

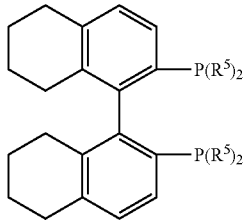

(II-C)

wherein $R^5$ is the same as defined above,
an optically active bidentate phosphine ligand represented by formula (II-D):

[Chemical formula 11]

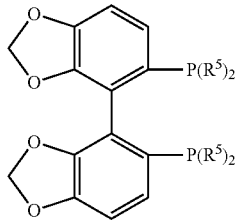

(II-D)

wherein $R^5$ is the same as defined above,
an optically active bidentate phosphine ligand represented by formula (II-E):

[Chemical formula 12]

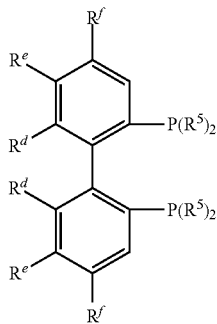

(II-E)

wherein $R^5$ is the same as defined above, $R^d$ represents a C1 to C6 alkyl group, C1 to C6 alkoxy group, halogen atom or trifluoromethyl group, $R^e$ represents a hydrogen atom, C1 to C6 alkyl group, C1 to C6 alkoxy group or halogen atom, and $R^f$ represents a hydrogen atom, C1 to C6 alkyl group or C1 to C6 alkoxy group,
an optically active bidentate phosphine ligand represented by formula (II-F):

[Chemical formula 13]

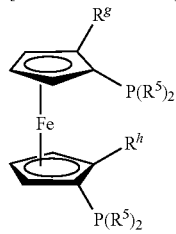

(II-F)

wherein $R^5$ is the same as defined above, $R^g$ represents a hydrogen atom or an unsubstituted or substituted C1 to C6 alkyl group, and $R^h$ represents a hydrogen atom or an unsubstituted or substituted C1 to C6 alkyl group, and
an optically active bidentate phosphine ligand represented by formula (II-G):

[Chemical formula 14]

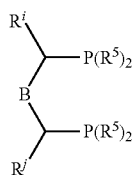

(II-G)

wherein $R^5$ is the same as defined above, each of $R^i$ and $R^j$ independently represents an unsubstituted or substituted C1 to C6 alkyl group or an unsubstituted or substituted C6 to C18 aryl group, or alternatively, $R^i$ and $R^j$ may be bonded together to form a ring, and B represents a single bond or an unsubstituted or substituted C1 to C6 alkylene group, (5) the method for producing an optically active aminoalcohol compound described in (2) or (3) above, wherein within the ruthenium compound represented by formula (I), the optically active bidentate phosphine ligand represented by formula (II) is an optically active bidentate phosphine ligand represented by formula (II-A):

[Chemical formula 15]

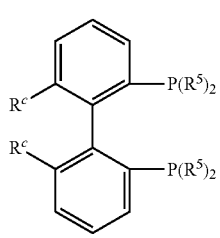

(II-A)

wherein $R^c$ represents a C1 to C6 alkyl group, C1 to C6 alkoxy group, halogen atom or trifluoromethyl group, and $R^5$ is the same as defined above, (6) the method for producing an optically active aminoalcohol compound described in (5) above, wherein the optically active bidentate phosphine ligand represented by formula (II-A) is 2,2'-bis[bis(3,5-dimethylphenyl)phosphanyl]-6,6'-dimethyl-1,1'-biphenyl, or (7) the method for producing an optically active aminoalcohol compound described in any one of (2) to (6) above, wherein within the ruthenium compound represented by formula (I), the optically active diamine ligand is 1,1-bis(4-methoxyphenyl)-2-isopropyl-1,2-ethanediamine, 1,2-diphenyl-1,2-ethanediamine, or 1,2-diaminocyclohexane.

The ruthenium compound according to the present invention is preferably:

(8) a ruthenium compound represented by formula (I-A):

[Chemical formula 16]

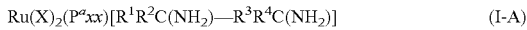

$$Ru(X)_2(P^a xx)[R^1R^2C(NH_2)-R^3R^4C(NH_2)] \quad (I\text{-}A)$$

wherein X represents a halogen atom,
$P^a xx$ represents an optically active bidentate phosphine ligand represented by formula (II-A):

[Chemical formula 17]

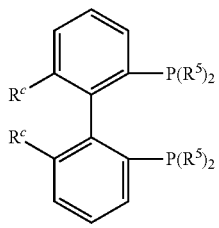

(II-A)

wherein $R^c$ represents a C1 to C6 alkyl group, C1 to C6 alkoxy group, halogen atom or trifluoromethyl group, and $R^5$ represents a phenyl group that has substituents, represented by formula (III):

[Chemical formula 18]

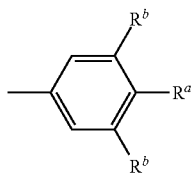

(III)

wherein $R^a$ represents a hydrogen atom, halogen atom, C1 to C6 alkyl group, C1 to C6 alkoxy group or C6 to C18 aryl group, and $R^b$ represents a halogen atom, C1 to C6 alkyl group, C1 to C6 alkoxy group or C6 to C18 aryl group, and $R^1R^2C(NH_2)-R^3R^4C(NH_2)$ represents an optically active diamine ligand, in which each of $R^1$ to $R^4$ independently represents a hydrogen atom, unsubstituted or substituted C1 to C20 alkyl group, unsubstituted or substituted C2 to C20 alkenyl group, unsubstituted or substituted C3 to C8 cycloalkyl group, unsubstituted or substituted C4 to C8 cycloalkenyl group, unsubstituted or substituted C6 to C18 aryl group, or unsubstituted or substituted C7 to C18 aralkyl group, and either of $R^1$ and $R^2$ may be bonded to either of $R^3$ and $R^4$ to form a ring, (9) the ruthenium compound described in (8) above, wherein within the ruthenium compound represented by formula (I-A), the optically active bidentate phosphine ligand represented by formula (II-A) is 2,2'-bis[bis(3,5-dimethylphenyl)phosphanyl]-6,6'-dimethyl-1,1'-biphenyl, or

(10) the ruthenium compound described in (8) or (9) above, wherein within the ruthenium compound represented by formula (I-A), the optically active diamine ligand is 1,1-bis(4-methoxyphenyl)-2-isopropyl-1,2-ethanediamine, 1,2-diphenyl-1,2-ethanediamine, or 1,2-diaminocyclohexane.

EFFECT OF THE INVENTION

As illustrated in the examples below, the ruthenium compound of the present invention enables an optically active aminoalcohol compound to be produced from an α-aminoketone compound with high stereoselectivity and high yield.

BEST MODE FOR CARRYING OUT THE INVENTION (1) Ruthenium Compound

The compound represented by formula (I) according to the present invention is described below in detail.
In formula (I):

[Chemical formula 19]

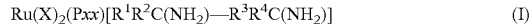

$$Ru(X)_2(Pxx)[R^1R^2C(NH_2)-R^3R^4C(NH_2)] \quad (I)$$

X represents a "halogen atom" such as a fluorine, chlorine, bromine or iodine atom.
Pxx represents an optically active bidentate phosphine ligand represented by formula (II).

[Chemical formula 20]

$$P(R^5)_2\text{-}A\text{-}P(R^5)_2 \quad (II)$$

In formula (II), $R^5$ represents a phenyl group that has substituents, represented by formula (III) below.

[Chemical formula 21]

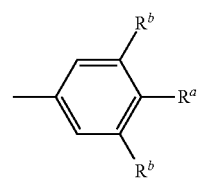

(III)

In this formula, $R^a$ represents a hydrogen atom, halogen atom, C1 to C6 alkyl group, C1 to C6 alkoxy group or C6 to C18 aryl group, and $R^b$ represents a halogen atom, C1 to C6 alkyl group, C1 to C6 alkoxy group or C6 to C18 aryl group.

In formula (II), A represents a divalent organic group. The divalent organic group is a general description that represents all divalent functional groups containing 2 to 60 carbon atoms, which may also include from 1 to 30 hetero atoms selected independently from among oxygen, nitrogen and sulfur. Examples of the divalent organic group include C1 to C8 alkyl groups, divalent organic groups formed from a C6 to C18 aryl group such as a biphenyl group or binaphthalenyl group, and divalent organic groups formed from a hetero ring such as pyrrolidine or a bipyridinyl group. Further, ferrocene, which has two cyclopentadienyl anion ligands bonded above and below an iron (II) ion, can also be used as the divalent organic group. These divalent organic groups may also have additional substituents.

The "C1 to C8 alkylene groups" include methylene, ethylene and trimethylene and the like.

Examples of the substituents mentioned above include the following.

The "halogen atoms" refer to fluorine, chlorine, bromine and iodine atoms and the like.

The "C1 to C6 alkyl groups" include methyl, ethyl, n-propyl, isopropyl, n-butyl, sec-butyl, t-butyl, n-pentyl, isopentyl, neopentyl, t-pentyl and hexyl groups and the like.

The "C1 to C6 alkoxy groups" include methoxy, ethoxy, n-propoxy, isopropoxy, n-butoxy, sec-butoxy and t-butoxy groups and the like.

The "C6 to C18 aryl groups" include both monocyclic and polycyclic C6 to C18 aryl groups, and in the case of the polycyclic aryl groups, include not only fully unsaturated groups, but also partially saturated groups. Specific examples include phenyl, naphthyl, azulenyl, indenyl, indanyl and tetralinyl groups and the like. A C6 to C10 aryl group is preferred.

Specific examples of the optically active bidentate phosphine ligand include phosphine ligands represented by general formula (II-B):

[Chemical formula 22]

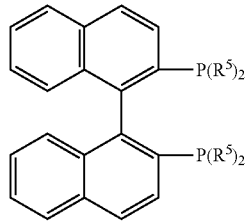

(II-B)

wherein $R^5$ represents a phenyl group that has substituents, represented by formula (III):

[Chemical formula 23]

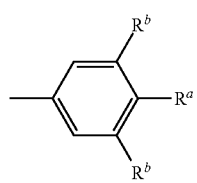

(III)

wherein $R^a$ represents a hydrogen atom, halogen atom, C1 to C6 alkyl group, C1 to C6 alkoxy group or C6 to C18 aryl group, and $R^b$ represents a halogen atom, C1 to C6 alkyl group, C1 to C6 alkoxy group or C6 to C18 aryl group.

$R^5$ is preferably a 3,5-dimethylphenyl group.

Furthermore, examples of other ligands besides those represented by general formula (II-B) include phosphine ligands represented by general formula (II-C):

[Chemical formula 24]

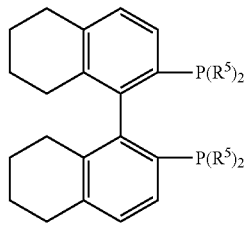

(II-C)

wherein $R^5$ is the same as defined above. $R^5$ is preferably a 3,5-dimethylphenyl group.

Furthermore, more examples of other ligands besides those represented by general formula (II-C) include phosphine ligands represented by general formula (II-D):

[Chemical formula 25]

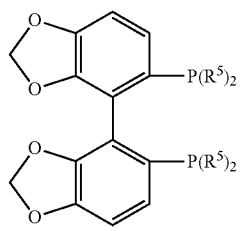

(II-D)

wherein $R^5$ is the same as defined above. $R^5$ is preferably a 3,5-dimethylphenyl group.

Furthermore, yet more examples of other ligands besides those represented by general formula (II-D) include phosphine ligands represented by general formula (II-E):

[Chemical formula 26]

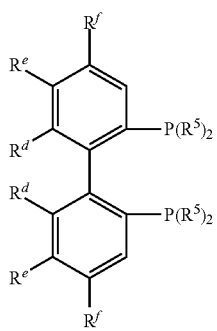

(II-E)

wherein $R^5$ is the same as defined above, $R^d$ represents a C1 to C6 alkyl group, C1 to C6 alkoxy group, halogen atom or trifluoromethyl group, $R^e$ represents a hydrogen atom, C1 to C6 alkyl group, C1 to C6 alkoxy group or halogen atom, and $R^f$ represents a hydrogen atom, C1 to C6 alkyl group or C1 to C6 alkoxy group. Specific examples of the "C1 to C6 alkyl group" and "C1 to C6 alkoxy group" for $R^d$, $R^e$ and $R^f$ include the same substituents as those exemplified above for the substituents within formula (III).

Specific examples include (4,4',6,6'-tetramethyl-5,5'-dimethoxybiphenyl-2,2'-diyl)-bis(bis(3,5-dimethylphenyl) phosphine), (4,4',6,6'-tetratrifluoromethylbiphenyl-2,2'- diyl)-bis(bis(3,5-dimethylphenyl)phosphine), (4,6-ditrifluoromethyl-4',6'-dimethyl-5'-methoxybiphenyl-2,2'-diyl)-bis(bis(3,5-dimethylphenyl)phosphine), and (4,4',5,5',6,6'-tetrahexamethoxybiphenyl-2,2'-diyl)-bis(bis(3,5-dimethylphenyl)phosphine).

Furthermore, a phosphine ligand represented by formula (II-A) is preferred:

[Chemical formula 27]

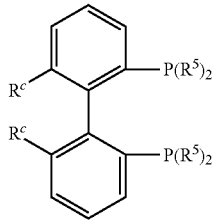

(II-A)

wherein $R^5$ is the same as defined above, and $R^c$ represents a C1 to C6 alkyl group, C1 to C6 alkoxy group, halogen atom or trifluoromethyl group. Specific examples of the "C1 to C6 alkyl group" for $R^c$ include the same substituents as those exemplified above for the substituents within formula (III). $R^5$ is preferably a 3,5-dimethylphenyl group.

Specific examples include 2,2'-bis[bis(3,5-dimethylphenyl)phosphanyl]-6,6'-dimethyl-1,1'-biphenyl, 2,2'-bis[bis(3,5-dimethylphenyl)phosphanyl]-6,6'-dimethoxy-1,1'-biphenyl, and 2,2'-bis[bis(3,5-dimethylphenyl)phosphanyl]-6,6'-dichloro-1,1'-biphenyl.

Furthermore, yet more examples of other ligands besides those represented by general formula (II-A) include optically active bidentate phosphine ligands represented by general formula (II-F):

[Chemical formula 28]

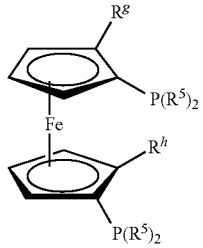

(II-F)

wherein $R^5$ is the same as defined above, $R^g$ represents a hydrogen atom or an unsubstituted or substituted C1 to C6 alkyl group, and $R^h$ represents a hydrogen atom or an unsubstituted or substituted C1 to C6 alkyl group. Specific examples of the "C1 to C6 alkyl group" for $R^g$ and $R^h$ include the same substituents as those exemplified above for the substituents within formula (III). $R^5$ is preferably a 3,5-dimethylphenyl group.

A specific example is 1',2-bis[bis(3,5-dimethylphenyl)phosphino]-ferrocenylethane.

Furthermore, yet more examples of other ligands besides those represented by general formula (II-F) include optically active bidentate phosphine ligands represented by general formula (II-G):

[Chemical formula 29]

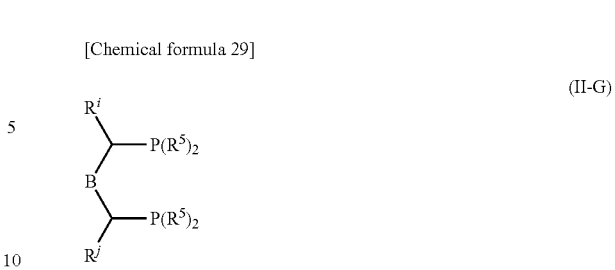

(II-G)

wherein $R^5$ is the same as defined above, each of $R^i$ and $R^j$ independently represents an unsubstituted or substituted C1 to C6 alkyl group or an unsubstituted or substituted C6 to C18 aryl group, $R^i$ and $R^j$ may be bonded together to form a ring, and B represents a single bond or an unsubstituted or substituted C1 to C6 alkylene group. Specific examples of the "C1 to C6 alkyl group" and "C6 to C18 aryl group" for $R^i$ and $R^j$ include the same substituents as those exemplified above for the substituents within formula (III). The "C1 to C6 alkylene group" includes methylene, ethylene and trimethylene and the like. $R^5$ is preferably a 3,5-dimethylphenyl group.

Specific examples include 2,3-bis(bis(3,5-dimethylphenyl)phosphino)butane, 1,2-bis(bis(3,5-dimethylphenyl)phosphino)propane, 5,6-bis(bis(3,5-dimethylphenyl)phosphino)-2-norbornene, 1-benzoyl-3,4-bis(bis(3,5-dimethylphenyl)phosphino)pyrrolidine, 2,4-bis(bis(3,5-dimethylphenyl)phosphino)pentane, and 2,3-o-isopropylidene-2,3-dihydroxy-1,4-bis(bis(3,5-dimethylphenyl)phosphino)butane.

Moreover, examples of other optically active bidentate phosphine ligands that can be used include (4,4',6,6'-tetramethyl-2,2'-biphenylene)-bis(bis(3,5-dimethylphenyl)phosphine), (3,3',6,6'-tetramethyl-2,2'-biphenylene)-bis(bis(3,5-dimethylphenyl)phosphine), (4,4'-difluoro-6,6'-dimethyl-2,2'-biphenylene)-bis(bis(3,5-dimethylphenyl)phosphine), (4,4'-bis(dimethylamino)-6,6'-dimethyl-2,2'-biphenylene)-bis(bis(3,5-dimethylphenyl)phosphine), 1,11-bis(bis(3,5-dimethylphenyl)phosphino)-5,7-dihydrobenzo[c,e]oxepin, and 7,7'-bis[bis(3,5-dimethylphenyl)phosphino]-3,3',4,4'-tetrahydro-4,4'-dimethyl-8,8'-bis(2H-1,4-benzoxazine). Further, ligands such as (5,5',6,6'-tetramethoxybiphenyl-2,2'-diyl)-bis(bis(3,5-dimethylphenyl)phosphine) may also be used.

Yet more examples include 1-tert-butoxycarbonyl-4-(bis(3,5-dimethylphenyl)phosphino)-2-(bis(3,5-dimethylphenyl)phosphino)methylpyrrolidine, 2,2',6,6'-tetramethoxy-4,4'-bis[bis(3,5-dimethylphenyl)phosphino]-3,3'-bipyridine, 7,7'-bis[bis(3,5-dimethylphenyl)phosphino]-2,2',3,3'-tetrahydro-1,1-spirobiindane, 1-(2-[bis(3,5-dimethylphenyl)phosphino]ferrocenyl)ethyl-bis-(3,5-dimethylphenyl)phosphine, and 4,12-bis[bis(3,5-dimethylphenyl)phosphino]-[2.2]-paracyclophane.

In formula (I), $R^1R^2C(NH_2)$—$R^3R^4C(NH_2)$ represents an optically active diamine ligand. In this ligand, each of $R^1$ to $R^4$ independently represents a hydrogen atom, unsubstituted or substituted C1 to C20 alkyl group, unsubstituted or substituted C2 to C20 alkenyl group, unsubstituted or substituted C3 to C8 cycloalkyl group, unsubstituted or substituted C4 to C8 cycloalkenyl group, unsubstituted or substituted C6 to C18 aryl group, or unsubstituted or substituted C7 to C18 aralkyl group, and either of $R^1$ and $R^2$ may be bonded to either of $R^3$ and $R^4$ to form a ring.

The "C1 to C20 alkyl group" of the "unsubstituted or substituted C1 to C20 alkyl group" includes methyl, ethyl, n-propyl, isopropyl, n-butyl, sec-butyl, t-butyl, n-pentyl, isopentyl, neopentyl, t-pentyl, hexyl, heptyl, octyl, nonyl, decyl and dodecyl and the like. A C1 to C6 alkyl group is preferred.

The "C2 to C20 alkenyl group" of the "unsubstituted or substituted C2 to C20 alkenyl group" includes ethenyl, n-propenyl, isopropenyl, n-butenyl, sec-butenyl, t-butenyl, 1,3-butadienyl, n-pentenyl, 2-pentenyl, 3-pentenyl, 2-hexenyl, 2-decenyl and 2-dodecenyl and the like. A C2 to C6 alkenyl group is preferred.

The "C3 to C8 cycloalkyl group" of the "unsubstituted or substituted C3 to C8 cycloalkyl group" describes an alkyl group having a cyclic portion, and includes cyclopropyl, cyclobutyl, cyclopentyl, cyclohexyl, cyclopropylmethyl, cyclopentylethyl and cyclohexylmethyl and the like.

The "C4 to C6 cycloalkenyl group" of the "unsubstituted or substituted C4 to C6 cycloalkenyl group" describes an alkenyl group having a cyclic portion, and includes 2-cyclobutenyl, 2-cyclohexenyl and 2-cyclopentenylmethyl and the like.

The "C6 to C18 aryl group" of the "unsubstituted or substituted C6 to C18 aryl group" is a monocyclic or polycyclic C6 to C18 aryl group, and in the case of polycyclic aryl groups, includes not only fully unsaturated groups, but also partially saturated groups. Examples include phenyl, naphthyl, azulenyl, indenyl, indanyl and tatralinyl and the like. A C6 to C10 aryl group is preferred.

The "C7 to C18 aralkyl group" of the "unsubstituted or substituted C7 to C18 aralkyl group" describes a group composed of an aryl group bonded to an alkyl group, and includes benzyl, phenethyl, phenylpropyl, phenylbutyl, phenylhexyl and naphthylmethyl and the like. A C6 to C10 aryl C1 to C6 alkyl group is preferred.

There are no particular limitations on the "substituent" relating to the "unsubstituted or substituted.", and any substituent that is chemically permissible may be used. Examples include halogen atoms such as a fluorine atom, chlorine atom, bromine atom and iodine atom; C1 to C6 alkyl groups such as a methyl group, ethyl group, n-propyl group and i-propyl group; C2 to C6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 4-hexenyl group and 5-hexenyl group; C2 to C6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 1-hexynyl group and 1,1-dimethyl-2-butynyl group; C1 to C6 alkoxy groups such as a methoxy group, ethoxy group and n-propoxy group; a nitro group; a cyano group; unsubstituted or substituted amino groups such as an amino group, methylamino group and dimethylamino group; unsubstituted or substituted aryl groups such as a phenyl group, p-trifluoromethylphenyl group and p-methoxyphenyl group; unsubstituted or substituted heterocyclic groups such as a 2-pyridyl group, 3-pyridyl group, 4-pyridyl group, 5-(2-chloro)pyridyl group and 6-(2-amino)pyridyl group; alkoxycarbonyl groups such as a methoxycarbonyl group, ethoxycarbonyl group, n-butoxycarbonyl group and t-butoxycarbonyl group; acyl groups such as an acetyl group and pivaloyl group; and a carboxyl group.

There are no particular limitations on the ring referred to "either of $R^1$ and $R^2$ may be bonded to either of $R^3$ and $R^4$ to form a ring", and any chemically permissible ring is possible. The ring is preferably a C5 to C8 hydrocarbon ring, and examples include cyclopentane-1,2-diyl, cyclohexane-1,2-diyl and 4-cyclohexene-1,2-diyl and the like.

In the diamine ligand, at least one of the carbon atoms C within $R^1R^2C(NH_2)$—$R^3R^4C(NH_2)$ is preferably optically active.

Specific examples of the diamine ligand include compounds formed with the combinations of substituents listed in the table below, although this is not limited thereto. In the table, the abbreviated symbols have the meanings shown below.

Ph: phenyl, c-Pr: cyclopropyl, c-He: cyclohexyl

TABLE 1

| No. | $R^1$ | $R^2$ | $R^3$ | $R^4$ |
|---|---|---|---|---|
| 1 | H | H | H | H |
| 2 | H | H | H | $CH_3$ |
| 3 | H | H | H | Ph |
| 4 | H | H | H | $CH_2$=CH |
| 5 | H | H | H | 4-$CH_3O$—Ph |
| 6 | H | H | H | c-He |
| 7 | H | H | H | 2-c-Hexenyl |
| 8 | H | H | H | $PhCH_2$ |
| 9 | H | H | H | n-$C_6H_{13}$ |
| 10 | H | H | $CH_3$ | $CH_3$ |
| 11 | H | H | Ph | Ph |
| 12 | H | H | 4-$CH_3O$—Ph | 4-$CH_3O$—Ph |
| 13 | H | H | 4-$CH_3$—Ph | 4-$CH_3$—Ph |
| 14 | H | H | c-He | c-He |
| 15 | H | H | $PhCH_2$ | $PhCH_2$ |
| 16 | H | H | n-$C_6H_{13}$ | n-$C_6H_{13}$ |
| 17 | H | H | $CH_2$=CH | $CH_2$=CH |
| 18 | H | H | 2-c-Hexenyl | 2-c-Hexenyl |
| 19 | H | H | $PhCH_2$ | $PhCH_2$ |
| 20 | H | $CH_3$ | H | $CH_3$ |
| 21 | H | Ph | H | Ph |
| 22 | H | 4-$CH_3O$—Ph | H | 4-$CH_3O$—Ph |
| 23 | H | 4-$CH_3$—Ph | H | 4-$CH_3$—Ph |
| 24 | H | c-He | H | c-He |
| 25 | H | $CH_2$=CH | H | $CH_2$=CH |
| 26 | H | $CH_2$=$CHCH_2$ | H | $CH_2$=$CHCH_2$ |
| 27 | H | c-Pr | H | c-Pr |
| 28 | H | c-He | H | c-He |
| 29 | H | 2-c-Hexenyl | H | 2-c-Hexenyl |
| 30 | H | $CH_3$ | H | Ph |
| 31 | H | $CH_3$ | $CH_3$ | $CH_3$ |
| 32 | H | Ph | Ph | Ph |
| 33 | H | $PhCH_2$ | $PhCH_2$ | $PhCH_2$ |
| 34 | H | 4-$CH_3O$—Ph | 4-$CH_3O$—Ph | 4-$CH_3O$—Ph |
| 35 | H | $CH_2$=CH | $CH_2$=CH | $CH_2$=CH |
| 36 | H | c-He | c-He | c-He |

TABLE 2

| No. | $R^1$ | $R^2$ | $R^3$ | $R^4$ |
|---|---|---|---|---|
| 37 | H | 2-c-Hexenyl | 2-c-Hexenyl | 2-c-Hexenyl |
| 38 | H | n-$C_6H_{13}$ | n-$C_6H_{13}$ | n-$C_6H_{13}$ |
| 39 | H | $CH_3$ | Ph | Ph |
| 40 | H | $CH_3$ | $CH_3$ | Ph |
| 41 | H | n-$C_3H_7$ | Ph | Ph |
| 42 | H | i-$C_3H_7$ | 4-$CH_3O$—Ph | 4-$CH_3O$—Ph |
| 43 | H | Ph | Ph | Ph |
| 44 | $CH_3$ | $CH_3$ | $CH_3$ | $CH_3$ |
| 45 | $CH_3$ | Ph | $CH_3$ | $CH_3$ |
| 46 | $CH_3$ | 4-$CH_3O$—Ph | $CH_3$ | $CH_3$ |
| 47 | $CH_3$ | 4-$CH_3$—Ph | $CH_3$ | $CH_3$ |
| 48 | $CH_3$ | c-He | $CH_3$ | $CH_3$ |
| 49 | $CH_3$ | $CH_2$=CH | $CH_3$ | $CH_3$ |
| 50 | $CH_3$ | $CH_2$=$CHCH_2$ | $CH_3$ | $CH_3$ |
| 51 | $CH_3$ | c-Pr | $CH_3$ | $CH_3$ |
| 52 | $CH_3$ | c-He | $CH_3$ | $CH_3$ |
| 53 | $CH_3$ | 2-c-Hexenyl | $CH_3$ | $CH_3$ |
| 54 | $CH_3$ | $C_2H_5$ | $CH_3$ | $C_2H_5$ |
| 55 | $CH_3$ | Ph | $CH_3$ | Ph |
| 56 | $CH_3$ | 4-$CH_3O$—Ph | $CH_3$ | 4-$CH_3O$—Ph |
| 57 | $CH_3$ | 4-$CH_3$—Ph | $CH_3$ | 4-$CH_3$—Ph |
| 58 | $CH_3$ | c-He | $CH_3$ | c-He |
| 59 | $CH_3$ | $CH_2$=CH | $CH_3$ | $CH_2$=CH |
| 60 | $CH_3$ | $CH_2$=$CHCH_2$ | $CH_3$ | $CH_2$=$CHCH_2$ |
| 61 | $CH_3$ | c-Pr | $CH_3$ | c-Pr |
| 62 | $CH_3$ | c-He | $CH_3$ | c-He |

TABLE 2-continued

| No. | $R^1$ | $R^2$ | $R^3$ | $R^4$ |
|---|---|---|---|---|
| 63 | $CH_3$ | 2-c-Hexenyl | $CH_3$ | 2-c-Hexenyl |
| 64 | H | $CH_2CH_2CH_2$ | | H |
| 65 | H | $CH_2CH_2CH_2CH_2$ | | H |
| 66 | H | $CH_2CH_2CH_2CH_2CH_2$ | | H |
| 67 | H | $CH_2CH=CHCH_2$ | | H |
| 68 | H | $CH_2CH_2CH_2$ | | $CH_3$ |
| 69 | H | $CH_2CH_2CH_2CH_2$ | | $CH_3$ |
| 70 | H | $CH_2CH=CHCH_2$ | | $CH_3$ |

Of these compounds, compounds of formula (I) in which at least one of $R^1$ to $R^4$ is an unsubstituted or substituted phenyl group, such as 1,1-bis(4-methoxyphenyl)-2-isopropyl-1,2-ethanediamine and 1,2-diphenyl-1,2-ethanediamine, or compounds of formula (I) in which either of $R^1$ and $R^2$ is bonded to either of $R^3$ and $R^4$ to form an alkyl ring, such as 1,2-diaminocyclopentane and 1,2-diaminocyclohexane, are preferred.

The ruthenium compound of formula (I) is preferably a compound represented by formula (I-A).

[Chemical formula 30]

$$Ru(X)_2(P^a xx)[R^1R^2C(NH_2)-R^3R^4C(NH_2)] \qquad (I\text{-}A)$$

$P^a xx$ represents an optically active bidentate phosphine ligand represented by formula (II-A). X and $R^1R^2C(NH_2)$—$R^3R^4C(NH_2)$ are the same as defined above.

Specific examples of the ruthenium compound of the present invention include {(S)-6,6'-bis[bis-(3,5-dimethylphenyl)-phosphanyl]-2,2'-dimethyl-biphenyl}ruthenium (II)dichloride (2S)-1,1-bis(4-methoxyphenyl)-2-isopropyl-1,2-ethanediamine, {(S)-6,6'-bis[bis-(3,5-dimethylphenyl)-phosphanyl]-2,2'-dimethyl-biphenyl}ruthenium(II) dichloride (1S,2S)-1,2-diphenyl-1,2-ethanediamine, and {(S)-6,6'-bis[bis-(3,5-dimethylphenyl)-phosphanyl]-2,2'-dimethyl-biphenyl}ruthenium(II)dichloride (1S,2S)-1,2-diaminocyclohexane.

(2) Method for Producing Ruthenium Compound

The ruthenium compound of the present invention can be produced by conventional methods (for example, see Patent Documents 2 and 3 above).

For example, the ruthenium compound may be produced using the method described below.

The starting material using in the method for producing the ruthenium compound may be a zero-valent, monovalent, divalent, trivalent, or higher valent ruthenium. Of these, the method that uses a divalent ruthenium complex disclosed in Angew. Chem. Int. Ed., 37, 1703 (1998) is particularly simple. In other words, a ruthenium compound represented by formula (I) can be produced by heating a solvent solution of a divalent ruthenium-halide complex and a bidentate phosphine ligand, and subsequently adding a diamine compound.

A method for producing the ruthenium compound using a divalent ruthenium-halide complex as a starting material is described below.

First, the divalent ruthenium-halide complex and the bidentate phosphine ligand of starting materials are heated and reacted within a solvent to obtain the corresponding phosphine-ruthenium-halide complex.

There are no particular limitations on the divalent ruthenium-halide complex used as a starting material, provided it is a ruthenium complex that has ligands that can be substituted with the bidentate phosphine ligand and the diamine ligand. Specific examples include diene-coordinated halogenated ruthenium compounds such as [ruthenium dichloride(norbornadiene)]polynuclear complex, [ruthenium dichloride(cyclooctadiene)]polynuclear complex and [bis (methylallyl)ruthenium(cyclooctadiene)]; and aromatic compound-coordinated halogenated ruthenium compounds such as [ruthenium dichloride(benzene)]dimer, [ruthenium dichloride(p-cymene)]dimer, [ruthenium dichloride(trimethylbenzene)]dimer and [ruthenium dichloride(hexamethylbenzene)]dimer.

The amount used of the bidentate phosphine ligand is typically within a range from 1 to 2 mols per 1 mol of the ruthenium-halide complex, and an equimolar amount is preferred.

Examples of solvents that can be used in this reaction include aromatic hydrocarbons such as toluene and xylene, aromatic hydrocarbons such as benzene, toluene and xylene; aliphatic hydrocarbons such as pentane and hexane; halogenated hydrocarbons such as dichloromethane, chloroform, trichloromethane, carbon tetrachloride and 1,2-dichloroethane; ethers such as diethyl ether, tetrahydrofuran (THF), 1,2-dimethoxyethane and 1,4-dioxane; alcohols such as methanol, ethanol, n-propanol, isopropanol, butanol and benzyl alcohol; amides such as N,N-dimethylformamide (DMF), N,N-dimethylacetamide, 1,3-dimethylimidazolidine, 1,3-dimethyl-2-imidazolidinone, N-methylpyrrolidone and hexamethylphosphortriamide (HMPT); nitriles such as acetonitrile and benzonitrile; and dimethylsulfoxide (DMSO). These solvents may be used individually, or two or more solvents may be used within a solvent mixture.

The amount used of the solvent is typically within a range from 1 to 100 ml per 1 g of the substrate, and is preferably within a range from 1 to 10 ml per 1 g of the substrate. The reaction temperature is typically within a range from 0 to 200° C., and is preferably within a range from room temperature to 100° C.

Subsequently, the obtained phosphine-ruthenium-halide complex and a diamine compound are reacted together to obtain the corresponding amine-phosphine-ruthenium-halide complex. The amount of the diamine compound used in this reaction is typically within a range from 1 to 2 mols per 1 mol of the phosphine-ruthenium-halide complex, and an equimolar amount is preferred. The reaction temperature is typically within a range from –100 to 200° C., and preferably from –10 to 50° C. Furthermore, the amine-phosphine-ruthenium-halide complex can also be obtained by first isolating the phosphine-ruthenium-halide complex, and then reacting the diamine compound with the isolated complex under the same conditions as those described above.

A ruthenium compound represented by formula (I) produced in the manner described above is useful as an asymmetric reduction catalyst for a carbonyl compound, and particularly for an α-aminoketone compound represented by formula (IV).

(3) Asymmetric Reduction Reaction of α-Aminoketone Compound

The ruthenium compound described above can be used for perforating an asymmetric reduction (hydrogenation) of a carbonyl compound to produce an optically active alcohol compound. The ruthenium compound is particularly ideal for performing an asymmetric reduction (hydrogenation) of an α-aminoketone compound to produce an optically active aminoalcohol compound such as an ephedrine compound.

The asymmetric reduction reaction is described below.

There are no particular limitations on the α-aminoketone compound used as the substrate for the asymmetric reduction reaction, provided it has a structure that is capable of undergoing an asymmetric reduction reaction. The α-aminoketone compound is preferably a compound represented by formula (IV):

[Chemical formula 31]

(IV)

wherein each of $R^{10}$ and $R^{11}$ independently represents an unsubstituted or substituted C1 to C6 alkyl group, or unsubstituted or substituted C6 to C18 aryl group, each of $R^{12}$ and $R^{13}$ represents a hydrogen atom, unsubstituted or substituted C1 to C6 alkyl group, unsubstituted or substituted C6 to C18 aryl group, $R^{14}CO$— group or $R^{14}OCO$— group, $R^{14}$ represents an unsubstituted or substituted C1 to C6 alkyl group, or unsubstituted or substituted C6 to C18 aryl group, and $R^{10}$ and $R^{11}$, and $R^{12}$ and $R^{13}$, may be respectively bonded together to form a ring.

In formula (IV), the "C1 to C6 alkyl group" of the "unsubstituted or substituted C1 to C6 alkyl group" includes methyl, ethyl, n-propyl, isopropyl, n-butyl, sec-butyl, t-butyl, n-pentyl, isopentyl, neopentyl, t-pentyl and hexyl and the like.

The "unsubstituted or substituted C6 to C18 aryl group" is a monocyclic or polycyclic aryl group, and in the case of a polycyclic aryl group, includes not only fully unsaturated groups, but also partially saturated groups. Examples include phenyl, naphthyl, azulenyl, indenyl, indanyl and tatralinyl and the like. A C6 to C10 aryl group is preferred.

$R^{14}$ within the "$R^{14}CO$— group or $R^{14}OCO$— group" represents an unsubstituted or substituted C1 to C6 alkyl group, or unsubstituted or substituted C6 to C18 aryl group, and the "C1 to C6 alkyl group" and "C6 to C18 aryl group" include the same groups as those described above.

The "$R^{14}CO$— group" includes C1 to C6 alkylcarbonyl groups such as acetyl, propionyl, butyryl and pivaloyl, as well as arylcarbonyl groups such as a benzoyl.

The "$R^{14}OCO$— group" includes C1 to C6 alkyloxycarbonyl groups such as methyloxycarbonyl, ethyloxycarbonyl and hexyloxycarbonyl, as well as aryloxycarbonyl groups such as phenyloxycarbonyl and 1-naphthyloxycarbonyl.

The "substituent" relating to the "unsubstituted or substituted" includes the same groups as those listed above for the "substituent" relating to the "unsubstituted or substituted" used in relation to the ruthenium compound represented by formula (I).

The "$R^{10}$ and $R^{11}$, and $R^{12}$ and $R^{13}$, may be respectively bonded together to form a ring" includes those cases where $R^{10}$ and $R^{11}$ are bonded together to form a hydrocarbon ring such as an alkyl ring or an alkenyl ring, and/or those cases where $R^{12}$ and $R^{13}$ are bonded together to faun a hetero ring such as a nitrogen-containing hydrocarbon ring.

The α-aminoketone compound that functions as the substrate is subjected to an asymmetric reduction in the presence of the ruthenium compound represented by formula (I), with a base added if desired, in the presence of a predetermined pressure of hydrogen gas or a hydrogen donor.

Further, in the present invention, the asymmetric reduction reaction may also be performed in situ, by first producing the ruthenium compound, either by adding the ruthenium complex (or ruthenium salt) that acts as the starting material for the ruthenium compound, a phosphorus compound, and a diamine compound separately to the reaction system, or by adding a ruthenium complex (or ruthenium salt) having a phosphine ligand and a diamine compound separately to the reaction system, if necessary together with an added base, and subsequently adding the substrate to the reaction system without isolating the ruthenium compound from the reaction system.

Although the amount used of the ruthenium compound represented by formula (I) that acts as a catalyst varies depending on the size of the reaction container and the catalytic activity, the amount is typically within a range from 1/50 to 1/2,000,000 mol, and preferably 1/500 to 1/500,000 mol per 1 mol of the α-aminoketone compound that functions as the reaction substrate.

Examples of the base used include organic bases such as triethylamine, diisopropylethylamine, pyridine, DABCO and DBU; metal alkoxides such as sodium methoxide, sodium ethoxide, potassium t-butoxide, magnesium methoxide and magnesium ethoxide; organolithium compounds such as n-butyl lithium; lithium amides such as LDA and lithium bistrimethylsilylamide; alkali metal hydroxides such as lithium hydroxide, sodium hydroxide and potassium hydroxide; alkaline earth metal hydroxides such as magnesium hydroxide and calcium hydroxide; alkali metal carbonates such as sodium carbonate and potassium carbonate; alkali metal hydrogen carbonates such as sodium hydrogen carbonate and potassium hydrogen carbonate; alkaline earth metal carbonates such as magnesium carbonate and calcium carbonate; and metal hydrides such as sodium hydride and calcium hydride.

The amount of base added is typically within a range from 2 to 500,000 mols, and preferably from 2 to 5,000 cools per 1 mol of the ruthenium compound.

There are no particular limitations on the solvent, provided it is capable of dissolving the substrate and the catalyst. Specific examples include alcohols such as methanol, ethanol, n-propanol, isopropanol, butanol and benzyl alcohol; aromatic hydrocarbons such as benzene, toluene and xylene; aliphatic hydrocarbons such as pentane and hexane; halogenated hydrocarbons such as dichloromethane, chloroform, trichloromethane, carbon tetrachloride and 1,2-dichloroethane; ethers such as diethyl ether, THF, 1,2-dimethoxyethane and 1,4-dioxane; amides such as DMF, N,N-dimethylacetamide, 1,3-dimethylimidazolidine, 1,3-dimethyl-2-imidazolidinone, N-methylpyrrolidone and HMPT; nitriles such as acetonitrile and benzonitrile; and DMSO. These solvents may be used individually, or two or more solvents may be used within a solvent mixture. Of these solvents, because the reaction product is an alcohol, the use of an alcohol solvent is preferred.

The amount used of the solvent varies depending on the solubility of the α-aminoketone compound and economic factors, and depending on the individual situation, the reaction may proceed either with no solvent, or in a state equivalent to very high dilution conditions. The amount of the solvent is usually within a range from 0.1 to 10,000 parts by weight, and preferably from 20 to 1,000 parts by weight, per 100 parts by weight of the α-aminoketone compound.

The hydrogen pressure is typically within a range from 1 to 200 atmospheres, and is preferably from 3 to 50 atmospheres. A hydrogen donor such as a hydrogen storage alloy or diimide may also be used, and the amount used is typically within a range from 1 to 100 equivalents relative to the α-aminoketone compound. The reaction temperature is typically within a range from −50 to 100° C., and preferably from 25 to 40° C.

Further, although the reaction time varies depending on the reaction conditions such as the concentration of the reaction substrate, the temperature and the pressure, the time is typically within a range from several minutes to several days. There are no particular limitations on the reaction type, and for example, either a batch reaction or continuous reaction type may be used.

Following completion of the reaction, typical organic synthetic chemistry techniques can be used to isolate and purify the target product. The structure of the target product can be determined using conventional techniques such as $^1$H-NMR, optical rotation measurements, liquid chromatography and gas chromatography.

EXAMPLES

The present invention is described below in further detail based on examples, although the present invention is not limited to these examples. The apparatus used for measurement of the physical properties in each of the examples are listed below.
(1) JMTC-300 (300 MHz, manufactured by JEOL, Ltd.)
(2) Measurement of optical rotation: Polarimeter JASCO DIP-360 (manufactured by JASCO Corporation)
(3) High-performance liquid chromatography: LC-10 Advp, SPD-10 Avp (manufactured by Shimadzu Corporation)

Example 1

Synthesis of Ruthenium Compounds

Example 1-1

Synthesis of {(S)-6,6'-bis[bis-(3,5-dimethylphenyl)-phosphanyl]-2,2'-dimethyl-biphenyl}ruthenium(II) dichloride (2S)-1,1-bis(4-methoxyphenyl)-2-isopropyl-1,2-ethanediamine complex A Schlenk tube was charged with deaerated dichloromethane (3 ml), {(S)-6,6'-bis[bis-(3,5-dimethylphenyl)-phosphanyl]-2,2'-dimethyl-biphenyl}ruthenium(II) dichloride DMF adduct (147 mg, 150 µmol) and (2S)-1,1-bis(4-methoxyphenyl)-2-isopropylethane-1,2-diamine (52 mg, 165 µmol), the resulting solution was stirred for 3 hours at room temperature, and the solvent was then removed. The reaction product was purified using a silica gel short column (eluent: diethyl ether) to obtain the target product (128 mg, 74%).
$^{31}$P-NMR (CDCl$_3$) d 43.4 (d, J$_{p-p}$=35.9 Hz), 46.6 (d, J$_{p-p}$=35.9 Hz)
[a]$_D^{29}$=−175° C. (c=1.01, CHCl$_3$)

Example 1-2

Synthesis of {(S)-6,6'-bis[bis-(3,5-dimethylphenyl)-phosphanyl]-2,2'-dimethyl-biphenyl}ruthenium(II) dichloride (1S,2S)-1,2-diphenyl-1,2-ethanediamine complex With the exception of using (1S,2S)-1,2-diphenyl-1,2-ethanediamine instead of (2S)-1,1-bis(4-methoxyphenyl)-2-isopropylethane-1,2-diamine, the same method as Example 1-1 was used to react {(S)-6,6'-bis[bis-(3,5-dimethylphenyl)-phosphanyl]-2,2'-dimethyl-biphenyl}ruthenium(II)dichloride DMF adduct (91.8 mg, 94 mmol) and (1S,2S)-1,2-diphenyl-1,2-ethanediamine (22 mg, 104 mmol) to obtain the target product (71.2 mg, 72%).

$^{31}$P-NMR (CDCl$_3$) d 44.8
[a]$_D^{29}$=−143° C. (c=1.01, CHCl$_3$)

Example 2

Synthesis of (1S,2S)-1-phenyl-2-(N-methyl-N-benzoylamino)-1-propanol

Example 2-1

Under an Ar atmosphere, a 100 ml autoclave was charged with 1-phenyl-2-(N-methyl-N-benzoyl)aminopropan-1-one (534 mg, 2 mmol), {(S)-6,6'-bis[bis-(3,5-dimethylphenyl)-phosphanyl]-2,2'-dimethyl-biphenyl}ruthenium(II)dichloride DMF adduct (2 mg, 2 mmol, S/C=1,000), (2S)-1,1-bis(4-methoxyphenyl)-2-isopropylethane-1,2-diamine (0.8 mg, 2.5 µmol) and 2-propanol (2 ml), the resulting solution was stirred for 30 minutes, $^t$BuOK (1M 2-propanol solution, 60 µl, 60 µmol) was added, and hydrogen was introduced to raise the pressure to 1 MPa. Following the resulting solution was stirred for 16 hours at 25° C., the reaction mixture was concentrated, and $^1$H-NMR measurement of the crude product revealed that the starting materials had been completely consumed, and that the obtained (1S,2S)-1-phenyl-2-(N-methyl-N-benzoylamino)-1-propanol had a diastereomeric ratio of syn:anti>20:1 (the signal for the anti isomer was not observed). The crude product was purified by silica gel column chromatography (eluent: hexane/ethyl acetate=1/1, 1/2), yielding 509 mg (95%) of the target compound. The enantiomeric excess was determined by HPLC (column: Daicel CHIRALPAK OJ-H), and was >99% ee.

Example 2-2

With the exception of setting S/C=10,000, the target product was obtained in the same manner as Example 2-1.
S/C: 10,000
Initial hydrogen pressure: 6 MPa
Reaction time: 16 hours
Conversion rate: 100%
syn:anti: >20:1
Enantiomeric excess: 99% ee Example 2-3

With the exception of using (1S,2S)-1,2-diphenyl-1,2-ethanediamine instead of (2S)-1,1-bis(4-methoxyphenyl)-2-isopropylethane-1,2-diamine, the target product was obtained in the same manner as Example 2-1.
S/C: 1,000
Initial hydrogen pressure: 1 MPa
Reaction time: 16 hours
Conversion rate: 100%
syn:anti: >20:1
Enantiomeric excess: 95% ee Example 2-4

Under an Ar atmosphere, a 100 ml autoclave was charged with 1-phenyl-2-(N-methyl-N-benzoyl)aminopropan-1-one (534 mg, 2 mmol), {(S)-6,6'-bis[bis-(3,5-dimethylphenyl)-phosphanyl]-2,2'-dimethyl-biphenyl}ruthenium(II)dichloride (2S)-1,1-bis(4-methoxyphenyl)-2-isopropyl-1,2-ethanediamine complex (2 mg, 2 µmmol, S/C 1,000), 2-propanol (2 ml) and $^t$BuOK (1M 2-propanol solution, 60 µl, 60 µmol), hydrogen was introduced to raise the pressure to 1 MPa, and the solution was stirred for 16 hours at 25° C.

Purification and analysis of the target product was performed using the same methods as those described in Example 2-1 (isolated yield: 99%).
Conversion rate: 100%
syn:anti: >20:1
Enantiomeric excess: >99% ee

Example 2-5

With the exception of using {(S)-6,6'-bis[bis-(3,5-dimethylphenyl)-phosphanyl]-2,2'-dimethyl-biphenyl}ruthenium(II)dichloride (1S,2S)-1,2-diphenyl-1,2-ethanediamine complex as the Ru complex, the target product was obtained in the same manner as Example 2-1.
Conversion rate: 100%
syn:anti: >20:1
Enantiomeric excess: 95% ee

Example 2-6

With the exception of using {(S)-6,6'-bis[bis-(3,5-dimethylphenyl)-phosphanyl]-2,2'-dimethyl-biphenyl}ruthenium(II)dichloride (1S,2S)-1,2-diphenyl-1,2-ethanediamine complex as the Ru complex, the target product was obtained in the same manner as Example 2-4 (isolated yield: 98%).
S/C: 1,000
Conversion rate: 100%
syn:anti: >20:1 (NMR)
Enantiomeric excess: 95% ee

Example 2-7

With the exception of using (S)-1,1'-binaphthyl-2,2'-bis-[di-(3,5-xylyl)]phosphine ruthenium(II)dichloride (2S)-1,1-bis(4-methoxyphenyl)-2-isopropyl-1,2-ethanediamine complex, the target product was obtained in the same manner as Example 2-4.
((S)-1,1'-binaphthyl-2,2'-bis-[di-(3,5-xylyl)]phosphine is abbreviated as (S)-Xyl BINAP)
S/C: 1,000
Initial hydrogen pressure: 1.2 MPa
Reaction time: 16 hours
Conversion rate: 100%
syn:anti: >99:1 (HPLC)
Enantiomeric excess: >99% ee

Example 2-8

With the exception of using (S)-1,1'-binaphthyl-2,2'-bis-[di-(3,5-xylyl)]phosphine ruthenium(II)dichloride (1S,2S)-1,2-diphenyl-1,2-ethanediamine complex, the target product was obtained in the same manner as Example 2-4 (isolated yield: 94%).
S/C: 1,000
Initial hydrogen pressure: 1.2 MPa
Reaction time: 16 hours
Conversion rate: 100%
syn:anti: >99:1 (HPLC)
Enantiomeric excess: 98% ee

Example 2-9

With the exceptions of setting S/C=5,000, and using (S)-6,6'-dimethyl-1,1'-binaphthyl-2,2'-bis-[di-(3,5-xylyl)]phosphine ruthenium(II)dichloride (2S)-1,1-bis(4-methoxyphenyl)-2-isopropyl-1,2-ethanediamine complex, the target product was obtained in the same manner as Example 2-4.
S/C: 5,000
Initial hydrogen pressure: 1.2 MPa
Reaction time: 1.5 hours
Conversion rate: 100%
syn:anti: >99:1 (HPLC)
Enantiomeric excess: >99% ee

Example 2-10

With the exception of using (S)-4,4'-bi-1,3-benzodioxole-5,5'-diyl-bis-[di(3,5-xylyl)phosphine]ruthenium(II)dichloride (2S)-1,1-bis(4-methoxyphenyl)-2-isopropyl-1,2-ethanediamine complex, the target product was obtained in the same manner as Example 2-4.
((S)-4,4'-bi-1,3-benzodioxole-5,5'-diyl-bis-[di(3,5-xylyl)phosphine] is abbreviated as (S)-Xyl SEGPHOS)
S/C: 1,000
Initial hydrogen pressure: 1 MPa
Reaction time: 16 hours
Conversion rate: 100%
syn:anti: >20:1 (NMR)
Enantiomeric excess: >99% ee

The invention claimed is:
1. A method for producing an optically active aminoalcohol compound, said method comprising performing a hydrogenation, in presence of a ruthenium compound represented by a formula (I):

[Chemical formula 1]

$$Ru(X)_2(Pxx)[R^1R^2C(NH_2)\text{—}R^3R^4C(NH_2)] \quad (I)$$

wherein X represents a halogen atom,
Pxx represents an optically active bidentate phosphine ligand represented by a formula (II):

[Chemical formula 2]

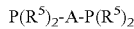

$$P(R^5)_2\text{-}A\text{-}P(R^5)_2 \quad (II)$$

wherein $R^5$ represents a phenyl group that has substituents, represented by a formula (III):

[Chemical formula 3]

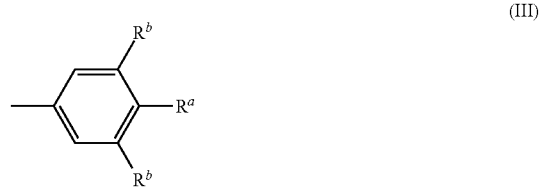

(III)

wherein $R^a$ represents a hydrogen atom, halogen atom, C1 to C6 alkyl group, C1 to C6 alkoxy group or C6 to C18 aryl group, and $R^b$ represents a halogen atom, C1 to C6 alkyl group, C1 to C6 alkoxy group or C6 to C18 aryl group,
and A represents a divalent organic group, and
$R^1R^2C(NH_2)\text{—}R^3R^4C(NH_2)$ represents an optically active diamine ligand, in which each of $R^1$ to $R^4$ independently represents a hydrogen atom, unsubstituted or substituted C1 to C20 alkyl group, unsubstituted or substituted C2 to C20 alkenyl group, unsubstituted or substituted C3 to C8 cycloalkyl group, unsubstituted or substituted C4 to C8 cycloalkenyl group, unsubstituted or substituted C6 to C18 aryl group, or unsubstituted or substituted C7 to C18 aralkyl group, and either of $R^1$ and $R^2$ may be bonded to either of $R^3$ and $R^4$ to form a ring, of an α-aminoketone compound represented by a formula (IV):

[Chemical formula 4]

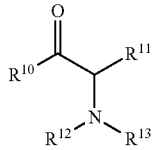

(IV)

wherein each of $R^{10}$ and $R^{11}$ independently represents an unsubstituted or substituted C1 to C6 alkyl group, or unsubstituted or substituted C6 to C18 aryl group, each of $R^{12}$ and $R^{13}$ represents a hydrogen atom, unsubstituted or substituted C1 to C6 alkyl group, unsubstituted or substituted C6 to C18 aryl group, $R^{14}CO$— group or $R^{14}OCO$— group, $R^{14}$ represents an unsubstituted or substituted C1 to C6 alkyl group, or unsubstituted or substituted C6 to C18 aryl group, and $R^{10}$ and $R^{11}$, and $R^{12}$ and $R^{13}$, may be respectively bonded together to form a ring.

2. The method for producing an optically active aminoalcohol compound according to claim 1, wherein $R^{10}$ in said formula (IV) is an unsubstituted or substituted phenyl group.

3. The method for producing an optically active aminoalcohol compound according to claim 1 or 2, wherein within said ruthenium compound represented by said formula (I), said optically active bidentate phosphine ligand represented by said formula (II) is any one of:

an optically active bidentate phosphine ligand represented by a formula (II-B):

[Chemical formula 5]

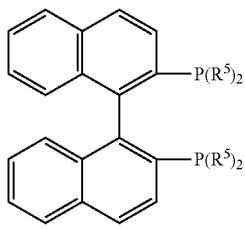

(II-B)

wherein $R^5$ is the same as defined above,
an optically active bidentate phosphine ligand represented by a formula (II-C):

[Chemical formula 6]

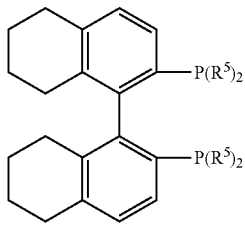

(II-C)

wherein $R^5$ is the same as defined above, an optically active bidentate phosphine ligand represented by a formula (II-D):

[Chemical formula 7]

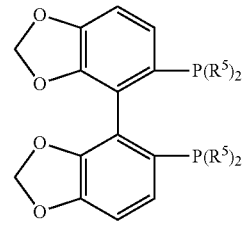

(II-D)

wherein $R^5$ is the same as defined above,
an optically active bidentate phosphine ligand represented by a formula (II-E):

[Chemical formula 8]

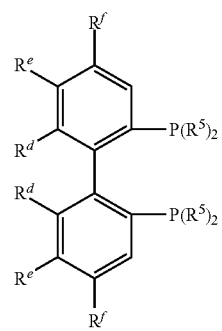

(II-E)

wherein $R^5$ is the same as defined above, $R^d$ represents a C1 to C6 alkyl group, C1 to C6 alkoxy group, halogen atom or trifluoromethyl group, $R^e$ represents a hydrogen atom, C1 to C6 alkyl group, C1 to C6 alkoxy group or halogen atom, and $R^f$ represents a hydrogen atom, C1 to C6 alkyl group or C1 to C6 alkoxy group, an optically active bidentate phosphine ligand represented by a formula (II-F):

[Chemical formula 9]

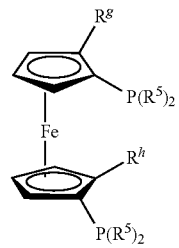

(II-F)

wherein $R^5$ is the same as defined above, $R^g$ represents a hydrogen atom or an unsubstituted or substituted C1 to C6 alkyl group, and $R^h$ represents a hydrogen atom or an unsubstituted or substituted C1 to C6 alkyl group, and an optically active bidentate phosphine ligand represented by a formula (II-G):

[Chemical formula 10]

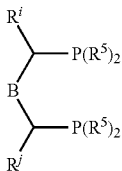

(II-G)

wherein $R^5$ is the same as defined above, each of $R^i$ and $R^j$ independently represents an unsubstituted or substituted C1 to C6 alkyl group or an unsubstituted or substituted C6 to C18 aryl group, $R^i$ and $R^j$ may be bonded together to form a ring, and B represents a single bond or an unsubstituted or substituted C1 to C6 alkylene group.

4. The method for producing an optically active aminoalcohol compound according to claim 1 or 2, wherein within said ruthenium compound represented by said formula (I), said optically active bidentate phosphine ligand represented by said formula (II) is an optically active bidentate phosphine ligand represented by a formula (II-A):

[Chemical formula 11]

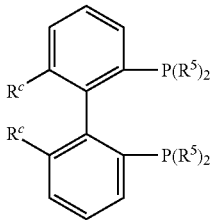

(II-A)

wherein $R^c$ represents a C1 to C6 alkyl group, C1 to C6 alkoxy group, halogen atom or trifluoromethyl group, and $R^5$ is the same as defined above.

5. The method for producing an optically active aminoalcohol compound according to claim 4, wherein said optically active bidentate phosphine ligand represented by said formula (II-A) is 2,2'-bis[bis(3,5-dimethylphenyl)phosphanyl]-6,6'-dimethyl-1,1'-biphenyl.

6. The method for producing an optically active aminoalcohol compound according to any one of claims 1 to 2, wherein within said ruthenium compound represented by said formula (I), said optically active diamine ligand is 1,1-bis(4-methoxyphenyl)-2-isopropyl-1,2-ethanediamine, 1,2-diphenyl-1,2-ethanediamine, or 1,2-diaminocyclohexane.

7. The method for producing an optically active aminoalcohol compound according to claim 3, wherein within said ruthenium compound represented by said formula (I), said optically active diamine ligand is 1,1-bis(4-methoxyphenyl)-2-isopropyl-1,2-ethanediamine, 1,2-diphenyl-1,2-ethanediamine, or 1,2-diaminocyclohexane.

8. The method for producing an optically active aminoalcohol compound according to claim 4, wherein within said ruthenium compound represented by said formula (I), said optically active diamine ligand is 1,1-bis(4-methoxyphenyl)-2-isopropyl-1,2-ethanediamine, 1,2-diphenyl-1,2-ethanediamine, or 1,2-diaminocyclohexane.

9. The method for producing an optically active aminoalcohol compound according to claim 5, wherein within said ruthenium compound represented by said formula (I), said optically active diamine ligand is 1,1-bis(4-methoxyphenyl)-2-isopropyl-1,2-ethanediamine, 1,2-diphenyl-1,2-ethanediamine, or 1,2-diaminocyclohexane.

* * * * *